United States Patent [19]

Desai

[11] Patent Number: 5,206,219
[45] Date of Patent: Apr. 27, 1993

[54] ORAL COMPOSITIONS OF PROTEINACEOUS MEDICAMENTS

[75] Inventor: Ashok J. Desai, Wilmington, N.C.

[73] Assignee: Applied Analytical Industries, Inc., Wilmington, N.C.

[21] Appl. No.: 797,221

[22] Filed: Nov. 25, 1991

[51] Int. Cl.$^5$ ............... A61K 9/10; A61K 9/48; A61K 9/66; A61K 37/02
[52] U.S. Cl. .................................. 514/3; 424/455; 424/463; 424/474; 424/490
[58] Field of Search .............. 514/3; 424/463, 455, 424/474, 490

[56] References Cited

U.S. PATENT DOCUMENTS

| | | | |
|---|---|---|---|
| 4,356,167 | 10/1982 | Kelly | 424/38 |
| 4,579,730 | 4/1986 | Kidron | 424/19 |
| 4,849,227 | 7/1989 | Cho, III | 424/498 |
| 4,880,835 | 11/1989 | Park | 514/570 |
| 4,910,021 | 3/1990 | Davis et al. | 424/456 |

FOREIGN PATENT DOCUMENTS

| | | | |
|---|---|---|---|
| 152345 | 8/1985 | European Pat. Off. | 514/969 |
| 87/05505 | 9/1987 | PCT Int'l Appl. | |
| 88/01213 | 2/1988 | PCT Int'l Appl. | |
| 90/01329 | 2/1990 | PCT Int'l Appl. | 514/3 |
| 90/03164 | 4/1990 | PCT Int'l Appl. | |
| 91/14454 | 10/1991 | PCT Int'l Appl. | 514/3 |

OTHER PUBLICATIONS

Ritschel Meth Find Exp Clin. Pharmacol. 13(3): 205–220 (1991).
Shichiri et al. Acta Diabet. Lat. 15: 175–183 (1978).

*Primary Examiner*—Shep K. Rose
*Attorney, Agent, or Firm*—William H. Edgerton

[57] ABSTRACT

Proteinaceous medicaments such as erythropoetin, insulin and calcitonin are formulated in a medium comprising a polyol pharmaceutical solvent combined as co-solvent with a lipid pharmaceutical solvent. The formulation is adapted for oral administration as a liquid as well as a filled hard or soft gelatin capsule. The preferred polyol solvent is polyethylene glycol/propylene glycol; the preferred lipid solvent is oleic acid.

13 Claims, No Drawings

ORAL COMPOSITIONS OF PROTEINACEOUS MEDICAMENTS

This invention relates to new oral dosage unit compositions of proteinaceous medicaments which are pharmaceutically elegant and which deliver the medicament, after oral administration, to the villi of the intestinal tract in the form of a microemulsion formed in situ. This invention also relates to methods of using these compositions.

BACKGROUND OF THE INVENTION

Biologically active compounds which are peptide or protein in nature have proved to be difficult to administer by the oral route to patients in need of treatment. The active material may be degraded by chemical or enzymatic agents in the gut such as the peptidases, strong acid, oxidizing agents and the like. Other factors may be physical instability, denaturation, surface adsorption, aggregation of proteins or precipitation in the gut.

Workers have sought a solution for this art problem in many ways, such as by means of liposome delivery (U.S. Pat. No. 4,356,167), lipid coating (U.S. Pat. No. 4,849,227, WO87/05505), use of peptidase inhibitors (U.S. Pat. No. 4,579,730), prodrugs, targeted microspheres (WO88/01213), coaccervate systems (U.S. Pat. No. 4,849,405) or, lately, emulsion formulations.

The use of oil/water emulsions for the oral delivery of peptides has received particular attention. Earlier work is summarized by M. Shichiri et al. (Acta diabet. lat. 15, 175 (1978)) and W. A. Ritschel (Meth. Find. Exp. Clin. Pharmacol. 13, 205 (1991)). The art terms and disclosures of the latter publication are incorporated herein by reference.

Y. W. Cho et al (PCT patent application WO 90/03164) discloses the use of oral proteinaceous compositions comprising oil/water emulsions which form chylomicra or deliver chylomicra to absorption sites in the gastrointestinal tracts. Cho discloses on page 9, line 23-29 that the hydrophilic phase (aqueous phase) may contain ethanol. In fact, the preferred embodiments, such as in the examples all contain a substantial quantity of ethanol in the aqueous layer of the emulsion. Also the emulsion is preferably adsorbed on particles before encapsulation (Example 3).

The prior art products have drawbacks in that oil/water emulsions are known in the art to have stability problems. The Cho products, when prepared as described in the PCT publication, have a disagreeable oily appearance which is not pharmaceutically elegant. Ethanol is also a well-known denaturant of many proteinaceous medicaments. The microfluidization process described by Cho also can denature the proteinaceous material due to heat and shear involved in the process.

DESCRIPTION OF THE INVENTION

This invention comprises a dosage unit pharmaceutical composition, adapted for oral administration, containing a liquid polyol solvent-lipid cosolvent medium and dissolved therein a dosage unit amount of a biologically active, proteinaceous medicament along with:

A. agents to form a microemulsion in the gastrointestinal tract at the sites of absorption, and B. agents which will stabilize and solubilize the contents of the pharmaceutical composition.

The active ingredients of the compositions described here are those accepted for use as medicaments and which have proteinaceous or peptidic chemical structures. Their dosage units are those accepted for medical purposes to be effective and non-toxic. The proteinaceous compound is either a pure protein or peptide or it can exhibit sugar residues in its structure. It may be isolated from natural sources, may be wholly or partially synthetic or may be of biotechnical origin. The number of amino acid units can range from 9 to 1,000 and the molecular weights from 1,000 to 100,000 daltons for certain large molecules.

Exemplary of active proteinaceous ingredients are erythropoietin, insulin, growth hormones, calcitonin, GCSF (growth colony stimulating factor), cyclosporine, vasopressin or its agonists and antagonists, t-PA or vampire bat plasminogen amplifier, urokinase, streptokinase, interferons or interleukins.

The active ingredients, in dosage unit quantities, are incorporated into a medium comprising a pharmaceutically acceptable polyol solvent and a pharmaceutically acceptable lipid solvent.

The polyol co-solvent is one or more of the group of polyhydric alcohols consisting of propylene glycol or a polyethylene glycol. Such polyethylene glycols are the polyalkylene glycol products such as those known in the art as the "PEG" series with chemical structures having 2 or 3 carbon atoms in the alkylene moiety and a mean molecular weight of 200 to 4,000.

The liquid lipid co-solvent is one or more of the group of fats or fat-like substances which act as solvents for ingredients of the composition and are liquid at room temperature. The lipid solvent must, of course, be suitable for human use and must be soluble in or freely miscible with the polyol co-solvent. Especially useful are the liquid saturated or unsaturated fatty acids such as oleic acid, isostearic acid, linoleic acid and linolenic acid.

The ratio of the polyol to lipid co-solvents in the medium is selected from the w/w ranges of 1 to 0.5 up to 1 to 5, preferably of 1 to 1.0 up to 1 to 3 and optimally of 1 to 1.6. Typical percentages in the media are about 15-35% of polyol to 30-60% of lipid.

The pre-emulsion medium is substantially non-aqueous and non-alcoholic. At times a minor quantity of water or buffer solution may conveniently be added to the polyol solvent system to dissolve or stabilize certain active ingredients. The aqueous content of the medium should be about 1-5% w/w. "Substantially" means as little as possible but no more than 5% w/w.

The preferred polyol co-solvent is a mixture of polyethylene glycol-propylene glycol in ratios of from 1-9 to 9-1 w/w, advantageously about 9-1.

This invention is not only intended for administration of proteinaceous materials but many other pharmacologically active agents (e.g. captopril, levodopa, propranolol, erythromycin, carbidopa, cimetidine, ranitidine, etc.) which are susceptible to degradation in the stomach and which lack the ability to be absorbed in the body. These active agents can also be administered in the same manner as described herein if they are indeed soluble in the pre-emulsion media described above.

The other components of the pre-emulsion compositions of this invention are agents which serve different functions: some stabilize the formulation; some stabilize or solubilize the active peptide medicament; others, most importantly, are designed to be part of the fatty globules formed by the ingested clear pre-emulsion medium when it reaches the point of absorption in the gut and forms a microemulsion. The lipid component of the solvent system may serve as solvent as well as a component of such fatty globules. These components are described hereafter and are incorporated into the pre-emulsion compositions as will be apparent to one skilled in the art from the following description and examples.

Phospholipids are one of the integral parts of the fatty globule membrane. It is also believed that these compounds act as precursors for the in vivo synthesis of lecithin at the human intestinal epithelium; lecithin thus forms a part of the membrane of the core of the globules. Chemically, phospholipids are glyceryl triesters in which one of the ester functions is an optionally substituted phosphoric acid.

Different types of phospholipids include diacyl phosphatidyl glycerols, diacyl phosphatidylcholines, diacyl phosphatidic acids, diacyl phosphatidyl ethanolamines. The sources of these types of phospholipids are synthetic or natural. Lecithin obtained from egg yolk or soya is a very suitable phospholipid. Other preferred phospholipids include dimyristoyl phosphatidyl choline, and dimyristoyl phosphatidic acid. The lipid phase capable of forming globules in the gastro-intestinal tract from the microemulsion has these additional ingredients:

Cholesterol or a suitable material that would form a fatty material matrix.

Lecithin or another mentioned phospholipid.

Lipophilic surfactant; e.g. long chain saturated/unsaturated fatty acid, which also could be optionally esterified with glycerol to form a mono-, di- or triglyceride. The ester formed can be glycerol or sorbitol esterified by saturated/unsaturated fatty acids namely oleic acid, linoleic acid, isostearic acid or any other suitable fatty acid.

Broad and preferred percentage ranges in the lipid co-solvent (which are w/v. w/w or even v/v) of the above mentioned ingredients are given below. It is to be noted that using the following optimal percentage ranges for the whole composition one could get the most stable formulation.

|  | Broad | Preferred | Optimal |
|---|---|---|---|
| Cholesterol | 0.5-25 | 1-10 | 4-6 |
| Lecithin | 0.5-40 | 1-15 | 8-12 |
| Lipophilic Surfactant | 0.5-30 | 1-12 | 4-8 |
| Lipid (Solvent Fatty Acid) | 0.5-95 | 5-75 | 30-50 |

The proteinaceous formulations using the optimal percentage ranges are preferred. The assumption using the above ranges is always that the percentage compositions do not exceed 100%.

Another highly desirable ingredient to be dissolved initially in the polyol phase is a high HLB surfactant. The HLB value greater than 15 usually suggests hydrophilic properties of the surfactant. HLB means hydrophilic lipophilic balance. The surfactant used would help to form the micro emulsion and also may help in promoting the formation of a complex between the proteinaceious material and the phospholipid. It is desirable that the surfactant used in the formulation be anionic or nonionic. Usually, there are many surfactants which are classified under the above mentioned categories and are pharmaceutically acceptable, safe and non-toxic. A list of surfactants with high HLB values is given. It is well recognized that these surfactants are esters of long chain fatty acids.

| Example of High HLB Surfactants | |
|---|---|
| Chemical | HLB |
| Esters of Polyethylene Glycol: | |
| Polyethylene Glycol Monostearate | 19.1 |
| Polyethylene Glycol Alkyl Ethers | — |
| Polyethylene Fatty Acid Esters: | |
| POE Mono and Di Stearate | |
| Polyoxyethylated Fatty Acids: | |
| POE(40) Lauric Acid | 17.9 |
| POE(40) Oleic Acid | 17.4 |
| POE(100) Oleic Acid | 18.8 |
| POE(50) Stearic Acid | 17.9 |
| POE(100) Stearic Acid | 18.8 |

The hydrophilic surfactant may be present in an amount up to 10% (w/w), preferably from 1-5% and typically 1-4% of the polyol solvent phase.

Another component of the formulation is a protease inhibitor. Either it can be used singly or in combination with one or more other protease inhibitors. The purpose of using the protease inhibitors is to inhibit or prevent the degradation of the proteinaceous material. Proteinaceous materials are digested in the GI tract by the enzymatic actions of trypsin, pepsin, chymotrypsin in the stomach and peptidase and amidase in the intestinal lumen. The enzymes are proteolytic in nature and have strong detergent properties. Thusly, they are very powerful in digesting proteins into amino acids for subsequent anabolism. Amino acids are often termed "building blocks" of the body. Thus, it is highly essential that the proteinaceous material which is being delivered orally be saved from the action of these enzymes. Thus, the proteolytic enzyme inhibitor becomes a vital ingredient in the formulation.

Very commonly used enzyme inhibitors are Aprotinin, and soybean trypsin inhibitor. Aprotinin is commercially available as Trasylol ®. Aprotinin is generally considered as safe and non-toxic compared to a wide variety of other enzyme inhibitors. The exact amount of Aprotinin to be used will depend upon the activity and the nature of the proteinaceous material. Generally speaking, 0.1-2% (w/w) of the polyol solvent phase is a range which can be used. Aprotinin can be added to the complex of the protein and the phospholipid or can be directly added to the polyol phase. Other inhibitors and their use in this field are described in U.S. Pat. No. 4,579,730 at column 3, lines 18-40.

An optional ingredient which can be added in the hydrophilic phase is a stabilizer for the formulation. For example, a number of well defined stabilizers for proteinaceious material include hydroxypropyl cellulose, hydroxypropyl methylcellulose, carboxy methylcellulose and methylcellulose. Organic acids and their salts like citric acid may also be utilized for stabilization of the protein. Since the proteinaceous material is added to the polyol, the stabilizer will also be added in the same solvent prior to mixing. The amount of the stabilizer is from 3-5% (w/w) of the polyol solvent phase.

In addition to a surfactant of high HLB value used in the polyol solvent, a low HLB surfactant in the lipid solvent may be used. The surfactants which would serve as a general aid in solubilization are not restricted to any particular HLB values. Useful aids include cholesterol, polysorbates, polyoxyethylene stearate, etc.

The exact amount to be used will be determined as simply enough to achieve proper solubilization and obtain a stable formulation. In accordance with this invention, it has been found suitable to use Polysorbate 80 in the lipid solvent.

Other adjuvants for preserving the formulation are common in pharmaceutical formulations. The useful agents are preservatives which could be further classified as antioxidants and antimicrobial agents. Long chain unsaturated fatty acids are particularly susceptible to oxidation. Also, other ingredients present in the lipid solvent are prone to oxidation and there is also a possibility of the oils getting rancid, thus it becomes highly desirable for the presence of anti-oxidants. Since the antioxidants need to be present in the lipid solvent, some oil soluble antioxidants like butylated hydroxyanisole, butylated hydroxytoluene, d-αtocopherol, propyl gallate, etc. are used. Typical antioxidant concentrations can be used which are usually a standard practice. Typically, these can be from 0.1-1.5% (w/w or w/v). If the need arises, higher concentrations can also be used. Hydrophilic antioxidants may also be added to the polyol solvent if necessary. Antimicrobial preservatives are very useful in preventing microbial growth. The most commonly used preservatives are parabens, sodium benzoate, benzylalkonium chloride, etc. The amounts can easily be determined by one skilled in the art.

The two co-solvents, each augmented by appropriate active ingredients, protective agents, stabilizing agents and/or fatty globule-forming agents, are mixed together using any mixing device available. The non-aqueous, non-ethanolic pre-emulsion composition of this invention is formed by mixing a certain ratio of polyol solution with lipid solution. The volume:volume ratio of the supplemented hydrophilic:hydrophobic cosolvents is in the range from 0.05 to 0.95, the preferred ratio being 0.3-0.7. A certain ratio can be selected based on the characteristics and the appearance chosen for the pre-emulsion solution. The resulting pre-emulsion composition is a clear liquid which may range from free-flowing to slightly viscous in nature. While the composition itself may be taken by mouth in dosage units, it is more palatable and efficacious to put a dosage unit of peptide in amounts known to art in a plain or enteric capsule which is administered orally from 2-5 times daily to a human or animal subject in need thereof.

The clear pre-emulsion solution, when taken orally, comes in contact with the digestive juices in the gastrointestinal tract, to form an in-situ micro-emulsion. This emulsion is formed at the villi and the microvilli which are the sites of absorption. This is the unique feature of the invention. The particle size of the emulsion droplets as seen microscopically is between 5-50 microns in diameter.

The pre-emulsion solution is encapsulated into a hard/soft gelatin capsule and the capsule is optionally coated with a pH resistant film which dissolves at a pH greater than 5.5. The gelatin capsule is most effective coated with enteric coating materials which are different polymers. It is observed that an effective enteric coating is obtained using an undercoat. The undercoating polymer can be hydroxypropyl methylcellulose, hydroxypropyl cellulose, hydroxypropyl ethylcellulose, polyvinylpyridone, etc. According to one variation of the invention, the pre-emulsion solution may be coated onto an adsorbent solid and the subsequent granules formed, such as by using rotary fluid bed techniques, and packed into a capsule. A variety of adsorbent materials like colloidal silicon dioxide, microcrystalline cellulose, lactose, alginic acid, etc. can be used. The capsule should be enteric coated so as to be protected in the stomach. Alternatively, the granules are enteric coated and packed into a capsule or compressed into a tablet. Thus, formulations which are obtained in accordance with the invention can be made in a wide variety of different ways, for example as a pre-emulsion solution into a soft gelatin/hard gelatin capsule, or granules formed by absorbing the solution onto a solid and packing the granules into a capsule which then is enteric coated, or enteric coating the granules obtained by the above process and packing into a hard gelatin capsule. The dosage unit prepared thus is administered orally 2-5 times daily to a human or animal patient in need thereof.

When the pre-emulsion solution is taken orally and is diluted with the intestinal fluids, an in-situ emulsion is formed at the villae and microvillae in the intestinal lumen of the GI tract. This in-situ emulsion has particle size in the range of 5-50 u. The in-situ emulsification process occurs in the small intestine namely the duodenum.

The pre-emulsion solution is encapsulated into a hard/soft gelatin capsule and the capsule is coated with a pH resistant film which dissolves at a pH greater than 5.5. Therefore, the passage of the capsule through the stomach is intact. The capsule opens after entry into the duodenum and an in-situ emulsion is formed to facilitate the absorption of the medicament as described in the prior art cited hereinabove.

Following are specific embodiments to teach the practice of the disclosed invention but not to limit its scope.

EXAMPLE 1

For this specific example, insulin as a biologically active proteinaceous material is used to obtain oral absorption from the delivery system. There is no heat involved which might denature the protein. There is also complete absence of alcohol which has been shown to denature peptides/proteins. The high HLB surfactant Myrj-52 ® is slowly dispersed into the mixture of polyethylene glycol 400 and propylene glycol. Once it dissolves, hydroxypropyl cellulose as a stabilizer is also added which is dispersed slowly into the above mixture. A separate solution of the proteinaceous material along with the phospholipid and the protease inhibitor is made in a portion of the above solvent mixture. The solution can then be added to the PEG/PG mixture at room temperature. The amount of any water is limited to 5% of the polyol solvent. When the water solution is used, citrate buffer is used to maintain the pH at a point where the protein is most stable. In this particular example, if insulin is used, it is suggested that the pH be maintained with a citrate buffer at or around 2.5. Separately, the ingredients of the lipid solvent are mixed together. Under gentle and constant stirring, the polyol solution is dispersed with the lipid solution.

In particular, insulin is delivered orally by the way of this invention. Insulin is a polypeptide consisting of 65 amino acids with an approximate molecular weight of 6,000 and is very widely used all over the world for the treatment and control of diabetes.

| Chemicals | % in the Respective Solvent | mg/ Capsule | Gm/Batch | % in the Final Formula |
| --- | --- | --- | --- | --- |
| Insulin | | 140 IU* | 118,860 IU | |
| Dimyristyl phosphatidyl choline | 0.027 | 0.047 | 0.04 | 0.0078 |
| Aprotinin** | 1.94 | 3.39 | 2.88 | 0.57 |
| Hydroxypropyl cellulose-LF | 2.14 | 3.76 | 3.18 | 0.64 |
| Poly-oxy 40 stearate | 2.14 | 3.76 | 3.18 | 0.64 |
| Polyethylene glycol 400 | 79.90 | 139.8 | 118.55 | 23.73 |
| Propylene glycol | 8.90 | 15.57 | 13.20 | 2.64 |
| Water/citrate buffer (pH adjustment) | 5.0 | 8.75 | 7.42 | 1.48 |
| Cholesterol | 7.64 | 31.2 | 26.46 | 5.30 |
| Tween 80 | 4.30 | 17.56 | 14.89 | 2.98 |
| Egg yolk lecithin | 15.45 | 63.1 | 53.51 | 10.71 |
| Glyceryl mono oleate | 6.83 | 27.9 | 23.66 | 4.74 |
| d-α tocopherol | 4.80 | 19.6 | 16.62 | 3.33 |
| Oleic acid | 61.0 | 249.1 | 211.24 | 42.29 |

Activity:
*Insulin: 26 IU = 1.0 mg
**Aprotinin: 7500 KIU = 1.0 mg

Manufacturing Procedure

The high HLB surfactant (Poly-oxy-40 stearate) is slowly dispersed into a mixture of polyethylene glycol and propylene glycol. Once it is dissolved, small amounts of hydroxypropyl cellulose are then added and dispersed into the same mixture. Insulin is dissolved in water and citric acid is dissolved in water for maintaining the pH at 2.5. The water solution is added to the polyethylene glycol mixture. In a separate beaker dissolve all the ingredients of the oil phase in oleic acid. Cholesterol is added slowly to achieve faster dissolution. Once both the phases are ready, the polyol solution is added slowly to lipid phase while mixing at low speed. The beaker should be preferably ice jacketed, since heat may be produced. Once the addition is achieved, a transparent yellowish brown solution is obtained.

The pre-emulsion solution is filled in a size 0 hard gelatin capsule and the capsule is sealed with a band of gelatin solution. The banding helps to coat the capsule uniformly. The capsule is then coated with a 10% hydroxypropyl methylcellulose solution as an undercoat. The amount of coat required is sufficient just enough to cover the capsule uniformly with a thin layer of the polymer coat. Usually, 3.5–4.5% weight gain of the capsule is a good indication of the amount required as an undercoat. Once the capsule is coated with an undercoat, enteric coating is applied. For enteric coating purposes, different polymers like hydroxypropyl methyl cellulose, hydroxypropyl methyl cellulose pthalate, cellulose acetate pthalate, etc. are used. Anionic copolymers which are based on methacrylic acid and methyl methycrate, commercially available as Eudragit ®, are also very suitable polymers for enteric coating purposes. The polymer is dissolved in organic solvents such as ethyl alcohol, methyl alcohol, acetone, isopropyl alcohol. A combination of two solvents can also be used. The amount of enteric coating solution required is 5–6% weight gain of the capsules from the original weight of the capsules before applying enteric coat. A typical enteric coating solution is made as follows:

| | |
| --- | --- |
| Methacrylic acid and methyl methycrate copolymer (polymer) | 10% w/w |
| Diethyl butyl pthalate (plasticizer) | 2% w/w |
| Acetone | 22% w/w |
| Isopropanol | 66% w/w |

Procedure

Mix acetone and isopropanol. Add the polymer slowly with constant mixing. Once the polymer is dissolved, add the plasticizer slowly and let it dissolve.

For a size 0 capsule the above mentioned enteric coating solution can be sprayed using fluidizing bed techniques. The fluid bed sprayer/dryer is operated with the following parameters:

| | |
| --- | --- |
| Flow Rate: | 1.5 mL/minute |
| Inlet Air Temp: | 25° C. |
| Outlet Air Temp: | 25° C. |
| Air Flap: | 35 |
| Atomizer: | 2.0 bar |

A batch size of about 500–525 capsules is optimum for effective uniform coating. A size 0 capsule after the enteric coating will typically have the following composition:

| | |
| --- | --- |
| Pre-emulsion Solution: | 0.589 g |
| Undercoat Polymer: | 0.027 g |
| Enteric Coat Polymer: | 0.032 g |
| | 0.648 g |

EXAMPLE 2

For the example listed below, erythropoietin is used as a proteinaceous material. Erythropoietin is a 165 amino acid glycoprotein of approximately 34,000 daltons. It is an endogenous protein which is involved in the production of red blood cells. It is indicated for the treatment of anemia associated with chronic renal failure, in AIDS patients and also to maintain or elevate the red blood cell level in the human body.

The procedure for making the formulation is same as listed previously in Example 1 except for pH adjustment. For erythropoietin, pH can be adjusted to 7–7.5 with a phosphate buffer. The amount of aqueous buffer solution would still be 5% of the hydrophilic phase. At a pH of 7.0–7.5, erythropoietin has its maximum stability. It is known that in formulating proteins the pH of the formulation should be distant from the isoelectric point of the protein which would not precipitate the protein from the solution.

| Chemicals | % in the Respective Solvent | mg/ Capsule | Gm/Batch | % in the Final Formula |
| --- | --- | --- | --- | --- |
| Erythropoietin | | 14,000 IU* | 5,936,000 IU | |
| Dimyristyl phosphatidyl choline | 0.027 | 0.047 | 0.020 | 0.008 |
| Aprotinin** | 1.94 | 3.42 | 1.45 | 0.58 |
| Hydroxypropyl cellulose-LF | 2.14 | 3.78 | 1.60 | 0.64 |
| Poly-oxy 40 | 2.14 | 3.78 | 1.60 | 0.64 |

-continued

| Chemicals | % in the Respective Solvent | mg/ Capsule | Gm/Batch | % in the Final Formula |
|---|---|---|---|---|
| stearate | | | | |
| Polyethylene glycol 400 | 79.90 | 141.1 | 59.83 | 23.95 |
| Propylene glycol | 8.90 | 15.72 | 6.66 | 2.67 |
| Phosphate buffer | 5.0 | 8.83 | 3.74 | 1.5 |
| Cholesterol | 7.64 | 31.49 | 13.35 | 5.35 |
| Egg yolk lecithin | 15.45 | 63.68 | 27.0 | 10.81 |
| d-α tocopherol | 4.80 | 19.78 | 8.39 | 3.36 |
| Oleic acid | 61.0 | 251.42 | 106.60 | 42.69 |
| Glyceryl mono oleate | 6.83 | 28.15 | 11.94 | 4.78 |
| Tween 80 | 4.30 | 17.72 | 7.51 | 3.01 |

Activity:
*Erythropoietin: 1000 IU = 8 ug
**Aprotinin: 7500 KIU = 1.0 mg

Manufacturing Procedure

The high HLB surfactant (Poly-oxy-40 stearate) is slowly dispersed into a mixture of polyethylene glycol and propylene glycol. Once it is dissolved, small amounts of hydroxypropyl cellulose are then added and dispersed into the same mixture. Erythropoietin is dissolved in the phosphate buffer/water/saline, along with Aprotinin and dimyristyl phosphatidyl choline. The aqueous solution is then added to the polyethylene glycol mixture at room temperature. The pH of the solution should be adjusted at 7.5 for maximum stability. In a separate beaker dissolve all the lipid-liking ingredients in oleic acid. Cholesterol is added slowly to achieve faster dissolution. Once both the phases are ready, the lipid solution is added slowly to polyol solution while mixing at low speed. The beaker should be preferably ice jacketed, since mixing produces heat. Once the mixing is achieved, a transparent yellowish brown pre-emulsion solution is obtained. The solution can be encapsulated into a capsule and coated according to Example 1.

EXAMPLE 3

Alternatively, bile salts or absorption enhancers are also used to enhance the absorption of orally administered proteins and peptides. Ingredients like sodium cholate, sodium deoxycholate, sodium taurocholate, sodium glycocholate are used to enhance the absorption. It is known to the art that some of the acids and their alkali salts are unsuitable for use in orally administered dosage forms due to the damage caused to the cells of the intestinal wall. Generally, the amounts of the bile acid/bile salts used are in the range of 1-20 mg/mL and 8-16 mg/mL often being the preferred concentration. The proteinaceous material in the following embodiment is human growth hormone which has an approximate molecular weight of 22,000 daltons. As a phospholipid, dimyristyl phosphatidic acid or its sodium salt can be used in this particular example. The high HLB surafactant used is Brij 35 ®. For the lipid solvent mixture, isostearic acid can be added instead of oleic acid. The lipophilic surfactant used in this example is sorbitan monooleate.

| Chemicals | % in the Respective Solvent | mg/ Capsule | Gm/Batch | % in the Final Formula |
|---|---|---|---|---|
| Human Growth Hormone | | 28 IU* | 11,872 IU | 1.83 |

-continued

| Chemicals | % in the Respective Solvent | mg/ Capsule | Gm/Batch | % in the Final Formula |
|---|---|---|---|---|
| Dimyristyl phosphatidic acid | 0.027 | 0.047 | 0.02 | 0.008 |
| Aprotinin** | 1.95 | 3.38 | 1.43 | 0.57 |
| Sodium Cholate | 2.0 | 3.47 | 1.47 | 0.59 |
| Poly-oxy-23 lauryl ether | 2.14 | 3.71 | 1.57 | 0.63 |
| Polyethylene glycol 400 | 79.0 | 138.60 | 58.77 | 23.53 |
| Propylene glycol | 7.9 | 13.70 | 5.81 | 2.33 |
| Water/pH adjuster | 5.0 | 8.67 | 3.68 | 1.47 |
| Cholesterol | 7.64 | 30.92 | 13.11 | 5.25 |
| Egg yolk lecithin | 15.45 | 62.53 | 26.51 | 10.61 |
| d-α tocopherol | 4.8 | 19.43 | 8.24 | 3.30 |
| Isostearic Acid | 61.0 | 246.90 | 104.68 | 41.92 |
| Sorbitan monooleate | 6.83 | 27.64 | 11.72 | 4.69 |
| Tween 80$^R$ | 4.30 | 17.40 | 7.38 | 2.95 |

Activity:
*Human Growth Hormone: 2.6 IU = 1.0 mg
**Aprotinin: 7500 KIU = 1.0 mg

Manufacturing Procedure

Polyoxy-23 lauryl ether (commercially available as Brij ® 35) is dispersed in the solvent mixture of polyethylene glycol 400 and propylene glycol. Sodium cholate is also separately dispersed in the mixture. A water solution containing recombinant human growth hormone, phospholipid and Aprotinin is then added to the above solvent mixture and the pH is adjusted to 7.5-7.8 with the help of phosphate buffer. The lipid solution is made separately in another beaker. To the oil solution, the polyol solution is added dropwise while mixing continuously. While mixing, it is suggested that the beaker be ice jacketed to prevent the denaturation of the protein in the formulation. A clear transparent liquid, which is called the pre-emulsion solution, is obtained after approximately 5 minutes of mixing at low speed. An in-situ emulsion can be made by mixing any ratio of the pre-emulsion solution with the simulated intestinal fluid.

EXAMPLE 4

Phospholipids are either used singularly or in combination with each other. For this particular example, human or salmon calcitonin is administered orally as a phospholipid complex in the polyol solvent.

When administering calcitonin, it is important that the pH be maintained at 2.0 or 2.5 with the help of a buffer. Calcitonin has maximum stability at pH 2.0.

| Chemicals | % in the Respective Solvent | mg/Capsule | Gm/Batch | % in the Final Formula |
|---|---|---|---|---|
| Salmon Calcitonin | | 500 IU | 212,000 IU | |
| Dimyristyl phosphatidic acid | 0.027 | 0.048 | 0.02 | 0.008 |
| Phosphatidyl choline | 0.027 | 0.048 | 0.02 | 0.008 |
| Hydroxypropyl cellulose-LF | 2.14 | 3.78 | 1.60 | 0.64 |
| Poly-oxy-40 stearate | 2.14 | 3.78 | 1.60 | 0.64 |
| Polyethylene glycol 400 | 79.8 | 140.97 | 59.77 | 23.93 |
| Propylene glycol | 8.8 | 15.55 | 6.59 | 2.64 |
| Citrate buffer/ | 5.0 | 8.83 | 3.74 | 1.50 |

-continued

| Chemicals | % in the Respective Solvent | mg/Capsule | Gm/Batch | % in the Final Formula |
|---|---|---|---|---|
| pH adjuster | | | | |
| Aprotinin | 1.95 | 3.44 | 1.46 | 0.58 |
| Cholesterol | 7.64 | 31.49 | 13.35 | 5.35 |
| Egg yolk lecithin | 15.45 | 63.69 | 27.0 | 10.81 |
| d-α tocopherol | 4.8 | 19.79 | 8.39 | 3.36 |
| Isostearic acid | 61.0 | 251.45 | 106.61 | 42.69 |
| Glyceryl monooleate | 6.83 | 28.15 | 11.94 | 4.78 |
| Tween 80$^R$ | 4.30 | 17.72 | 7.51 | 3.01 |

Manufacturing Procedure

The high HLB surfactant (Poly-oxy-40 stearate) is slowly dispersed into a mixture of polyethylene glycol and propylene glycol. Hydroxypropyl cellulose is also added in small amounts into the same solvent mixture. Salmon calcitonin can be dissolved in citrate buffer along with the phospholipids and Aprotinin or citric acid can be added in the water directly. The water solution is added to the solvent mixture with constant mixing. The pH of the polyol solution should be adjusted at 2.5 for maximum stability. Oil phase is made separately in another beaker. To the oil solution, the polyol solution is added slowly with constant homogenization. A clear transparent pre-emulsion composition is obtained. This solution can be filled into a capsule and coated with a suitable polymer according to Example 1.

EXAMPLE 5

Pre-Emulsion Solution Diluted with Simulated Intestinal Fluid

Objective: Record the percent transmittance of the pre-emulsion medium (from Example 1) in various ratios diluted with simulated intestinal fluid U.S.P.

Instrument: Beckman DU ®-37 spectrophotometer, 1 cm cell, Vanderkamp ® 600 six spindle dissolution tester.

Procedure: Pour 500 ml of simulated intestinal fluid into the dissolution vessel, set the paddle speed to 200 RPM. Let the fluid warm up to 37° C., then add 5 ml of pre-emulsion medium to the SIF. This is 1:100 ratio of dilution. Make different ratios of dilution of the pre-emulsion with the intestinal fluid. Pour 3-5 ml of sample from the dissolution vessel at 5.0 minute intervals for up to 60.0 minutes. The zero time reading is the percent transmittance of pre-emulsion medium before any addition of the simulated intestinal fluid.

Results

| Time in Minutes | % Transmittance at 800 nm | | | |
|---|---|---|---|---|
| | 1:50 | 1:100 | 1:200 | 1:400 |
| 0 | 92.1 | 78.6 | 91.3 | 92.1 |
| 5 | 0.6 | 5.4 | 30.4 | 56.3 |
| 10 | 0.6 | 5.7 | 29.0 | 59.3 |
| 15 | 0.54 | 5.7 | 29.8 | 57.6 |
| 20 | 0.54 | 5.7 | 28.8 | 57.6 |
| 25 | 0.47 | 6.4 | 32.1 | 59.1 |
| 30 | 0.47 | 6.6 | 31.8 | 57.9 |
| 35 | 0.40 | 6.1 | 31.7 | 56.6 |
| 40 | 0.40 | 6.7 | 32.9 | 60.8 |
| 45 | 0.40 | 6.3 | 34.6 | 59.7 |
| 50 | 0.40 | 6.0 | 33.4 | 59.9 |
| 55 | 0.40 | 6.1 | 34.0 | 53.6 |
| 60 | 0.34 | 6.0 | 33.0 | 57.6 |

Comments

The data show that the pre-emulsion solution is a transparent solution before the dilution with the intestinal fluid. At 800 nm the light transmitted is approximately 90%. Once the pre-emulsion solution is diluted with the intestinal fluid, an in-situ emulsion is formed and the percent light transmitted drops remarkably. As seen from the data, when the emulsion is more diluted, more light passes through it compared to when it is only diluted 50 times. When it is a concentrated emulsion it is opaque, and it gets more transparent and more light passes through it as the dilution increases. Microscopic studies have shown that a water in oil in water microemulsion is present after dilution with SIF.

What is claimed is:

1. A pharmaceutical enteric coated composition adapted for oral administration comprising:
   (a) a dosage unit of a protease inhibitor and of a proteinaceous medicament which is a member selected from the group consisting of erythropoietin, insulin, a growth hormone, calcitonin, growth colony stimulating factor, cyclosporine, vasopressin, a vasopressin agonist, a vasopressin antagonist, t-PA, vampire bat plasminogen amplifier, urokinase, streptokinase, interferon and interleukin each in a biologically effective, non-toxic quantity;
   (b) a phospholipid;
   (c) cholesterol;
   (d) a hydrophyllic or hydrophobic surfactant; and
   (e) a substantially non-aqueous, non-alcoholic pre-emulsion emulsifiable solution medium therefor comprising from 15 to 35% of a liquid polyol pharmaceutical solvent for said proteinaceous medicament which is selected from the group consisting of propylene glycol and a polyethylene glycol combined with from 30 to 60% of a liquid lipid pharmaceutical solvent for said proteinaceous medicament which is selected from the group consisting of oleic acid, isostearic acid, linoleic acid and linolenic acid.

2. A composition of claim 1 wherein the polyol solvent is polyethylene glycol and the lipid solvent is oleic acid.

3. A composition of claim 1 wherein the polyol solvent is polyethylene glycol/propylene glycol.

4. A composition of claim 1 wherein the phospholipid is lecithin.

5. A composition of claim 1 wherein the medicament is insulin.

6. A composition of claim 1 wherein the medicament is insulin, the polyol solvent is propylene glycol/polyethylene glycol 400, the lipid solvent is oleic acid and the phospholipid is lecithin.

7. A composition of claim 1 wherein a nontoxic, effective quantity of Aprotinin is present.

8. A composition of claim 1 wherein said composition is a filled enteric capsule.

9. A composition of claim 6 wherein said composition is a filled enteric capsule.

10. The method of administering a proteinaceous medicament orally to a subject in need thereof comprising administering a composition of claim 1 from 2-5 times daily.

11. In the preparation of an enteric coated pharmaceutical composition adapted for the oral administration of a protease inhibitor and of a proteinaceous medicament which is a member selected from the group consisting of erythropoietin, insulin, a growth hormone, calcitonin, growth colony stimulating factor, cyclosporine, vasopressin, a vasopressin agonist, a vasopressin antagonist, t-PA, vampire bat plasminogen amplifier, urokinase, streptokinase, interferon and interleukin each in a biologically effective, non-toxic quantity, the improvement comprising the incorporation into an enteric coated composition of a liquid medium containing said medicament which is a substantially non-aqueous, non-alcoholic mixture of a liquid polyol pharmaceutical solvent for said medicament selected from the group consisting of propylene glycol and a liquid polythylene glycol combined with a liquid lipid pharmaceutical solvent for said medicament which is selected from the group consisting of oleic acid, isostearic acid, linoleic acid and linolenic acid.

12. The improvement of claim 11 wherein said medicament is insulin.

13. The improvement of claim 12 wherein said medium comprises polyethylene glycol 400/propylene glycol and oleic acid.

* * * * *